United States Patent
Lin et al.

(10) Patent No.: US 6,752,882 B2
(45) Date of Patent: Jun. 22, 2004

(54) MEDICAL IMPLANT MADE OF BIOCOMPATIBLE LOW MODULUS HIGH STRENGTH TITANIUM-NIOBIUM ALLOY AND METHOD OF USING THE SAME

(75) Inventors: Jiin-Huey Chern Lin, 911 Tower Rd., Winnetka, IL (US) 60093; Chien-Ping Ju, 16 Pinewood Dr., Carbondale, IL (US) 62901; Chih-Min Lee, Kaohsiung (TW)

(73) Assignees: Jiin-Huey Chern LIN, Winnetka, IL (US); Chien-Ping Ju, Carbondale, IL (US)

(*) Notice: Subject to any disclaimer, the term of this patent is extended or adjusted under 35 U.S.C. 154(b) by 47 days.

(21) Appl. No.: 10/134,524

(22) Filed: Apr. 30, 2002

(65) Prior Publication Data

US 2002/0162608 A1 Nov. 7, 2002

Related U.S. Application Data

(63) Continuation-in-part of application No. 09/226,204, filed on Jan. 7, 1999, now Pat. No. 6,409,852.

(51) Int. Cl.$^7$ .............................................. C22C 14/00
(52) U.S. Cl. ...................... 148/421; 420/421; 420/417; 623/16.11; 623/23.53
(58) Field of Search .................... 148/421; 420/421, 420/417; 623/16.11, 23.53

(56) References Cited

U.S. PATENT DOCUMENTS

| | | | | |
|---|---|---|---|---|
| 5,205,984 A | * | 4/1993 | Rowe | 420/420 |
| 5,415,704 A | * | 5/1995 | Davidson | 148/316 |
| 5,906,692 A | * | 5/1999 | Bhowal et al. | 148/671 |

* cited by examiner

*Primary Examiner*—Andrew L Oltmans
(74) *Attorney, Agent, or Firm*—Bacon & Thomas

(57) ABSTRACT

A biocompatible binary titanium-niobium (Ti—Nb) alloy having a low modulus and a high strength, and containing α" phase as a major phase is disclosed. The binary Ti—Nb alloy contains 10–30 wt % of Nb, preferably 13–28 wt % of Nb, and the balance titanium, which is suitable for making a medical implant such as an orthopedic implant or dental implant.

4 Claims, 5 Drawing Sheets

MEDICAL IMPLANT MADE OF BIOCOMPATIBLE LOW MODULUS HIGH STRENGTH TITANIUM-NIOBIUM ALLOY AND METHOD OF USING THE SAME

CROSS-REFERENCE TO RELATED APPLICATION

The present application is a continuation-in-part application of U.S. Pat. application Ser. No. 09/226,204, filed Jan. 7, 1999, now U.S. Pat. No. 6,409,852, issued Jun. 25, 2002. The above-listed application Ser. No. 09/226,204 is commonly assigned with the present invention and the entire content of which is incorporated herein by reference.

FIELD OF THE INVENTION

The present invention is related to a biocompatible low modulus high strength titanium-niobium alloy, and in particular to a biocompatible Ti—Nb alloy having a major phase of $\alpha''$ suitable for making a medical implant.

BACKGROUND OF THE INVENTION

Titanium and titanium alloys have been popularly used in many medical applications due to their light weight, excellent mechanical performance and corrosion resistance. The relatively low strength commercially pure titanium (c.p. Ti) is currently used as dental implant, crown and bridge, as well as denture framework. With a much higher strength than c.p. Ti, Ti-6Al-4V alloy has been widely used in a variety of stress-bearing orthopedic applications, such as hip prosthesis and artificial knee joint. Moreover, the lower elastic modulus allows the titanium alloy to more closely approximate the stiffness of bone for use in orthopedic devices compared to alternative stainless steel and cobalt-chrome alloys in orthopedic implants. Thus, devices formed from the titanium alloy produce less bone stress shielding and consequently interfere less with bone viability.

Various attempts at providing low modulus, high strength titanium alloys for making medical implants with less stress shielding have been proffered by the prior art. There is still a need in the industry for a lower modulus and higher strength titanium alloys. In addition, studies have reported that the release of Al and V ions from the medical implants might cause some long-term health problems, for example the low wear resistance of Ti-6Al-4V alloy could accelerate the release of such harmful ions. Therefore, a titanium alloy free from potential harmful components is also an important goal of the present invention.

SUMMARY OF THE INVENTION

The present invention provides a biocompatible low modulus high strength titanium-niobium (Ti—Nb) alloy containing $\alpha''$ phase as a major phase and consisting essentially of 10–30 wt % of Nb, preferably 13–28 wt % of Nb, and the balance titanium.

The Ti—Nb alloy of the present invention may further comprises one or more incidental impurities selected from the group consisting of carbon, oxygen and nitrogen, wherein a total amount of said one or more incidental impurities is less than 1 wt %.

The present invention also discloses a medical implant made of the titanium-niobium alloy of the present invention.

Preferably, the medical implant of the present invention is an orthopedic implant.

Preferably, the medical implant of the present invention is a dental implant, dental crown, dental bridge or a denture framework.

The present invention further provides a method of treating a patient requiring bone or dental prosthesis comprising implanting the orthopedic implant or dental implant of the present invention into said patient.

BRIEF DESCRIPTION OF THE DRAWINGS

The invention will be described in conjunction with the following drawings wherein.

DETAILED DESCRIPTION OF THE PREFERRED EMBODIMENTS

In the present invention we have prepared Ti—Nb alloys having 5 wt % to 35 wt % of niobium (Nb). Each Ti—Nb alloy was prepared by using the same procedures except that the amounts of the components were different. A comprehensive preparation procedures of Ti—Nb alloy containing Nb 17.5 wt % together with the analysis of the Ti—Nb alloys will be described in the following examples, that are intended as illustrative only since numerous modifications and variations therein will be apparent to those skilled in the art.

EXAMPLES

Ti—Nb alloy containing 17.5 wt % of Nb and the balance Ti was prepared from a commercially pure titanium (c.p. Ti) bar, and niobium wire using a commercial arc-melting vacuum-pressure type casting system (Castmatic, Iwatani Corp., Japan). The melting chamber was first evacuated and purged with argon. An argon pressure of 1.5 kgf/cm² was maintained during melting. Appropriate amounts of the c.p. Ti bar and niobium wire (82.5 wt % Ti-17.5 wt % Nb) were melted in a U-shaped copper hearth with a tungsten electrode. The ingot was re-melted three times to improve chemical homogeneity.

Prior to casting, the ingot was re-melted again in an open-based copper hearth under an argon pressure of 1.5 kgf/cm². The molten alloy instantly dropped from the open-based copper hearth into a graphite mold located in a second chamber at room temperature because of the pressure difference between the two chambers.

Various Ti—Nb alloys were also prepared according to the aforesaid procedures. Table 1 lists the weight percentages of the starting metals in the preparation and the concentrations of the resultant alloys determined by EDS (energy dispersive spectroscopy).

TABLE 1

Niobium concentrations of Ti-Nb alloys prepared

| Sample code | Starting weight percentage of Nb | Nb concentration (wt %)* |
|---|---|---|
| Ti-5 Nb | 5 wt % | 5.08 ± 0.20 |
| Ti-10 Nb | 10 wt % | 10.32 ± 0.35 |
| Ti-15 Nb | 15 wt % | 13.66 ± 0.22 |
| Ti-17.5 Nb | 17.5 wt % | 17.97 ± 0.52 |
| Ti-20 Nb | 20 wt % | 20.76 ± 1.58 |
| Ti-22.5 Nb | 22.5 wt % | 22.37 ± 1.02 |
| Ti-25 Nb | 25 wt % | 24.09 ± 1.23 |
| Ti-27.5 Nb | 27.5 wt % | 26.65 ± 1.01 |
| Ti-30 Nb | 30 wt % | 29.09 ± 0.45 |
| Ti-35 Nb | 35 wt % | 35.72 ± 0.68 |

*All concentrations are averages of 5 measurements determined by EDS

Figure 1:
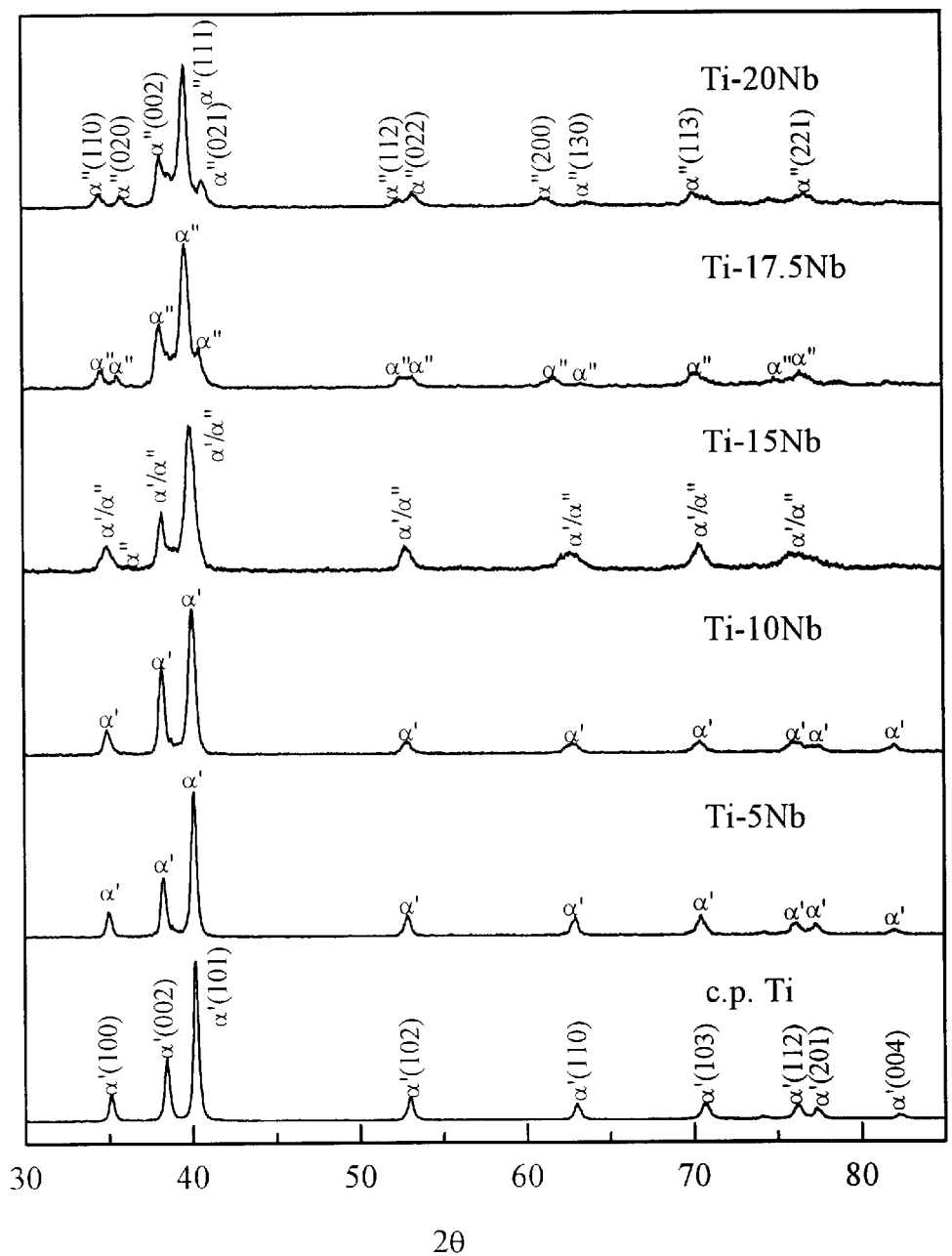
FIG. 1 shows X-ray diffraction spectra of the c.p. Ti and the binary Ti—Nb alloys of the present invention, Ti-5Nb, Ti-10Nb, Ti-15Nb, Ti-17.5Nb, Ti-20Nb, Ti-22.5Nb, Ti-25Nb, Ti-27.5Nb, Ti-30Nb, and Ti-35Nb, at a scanning speed of 1°/min.
Figure 1:
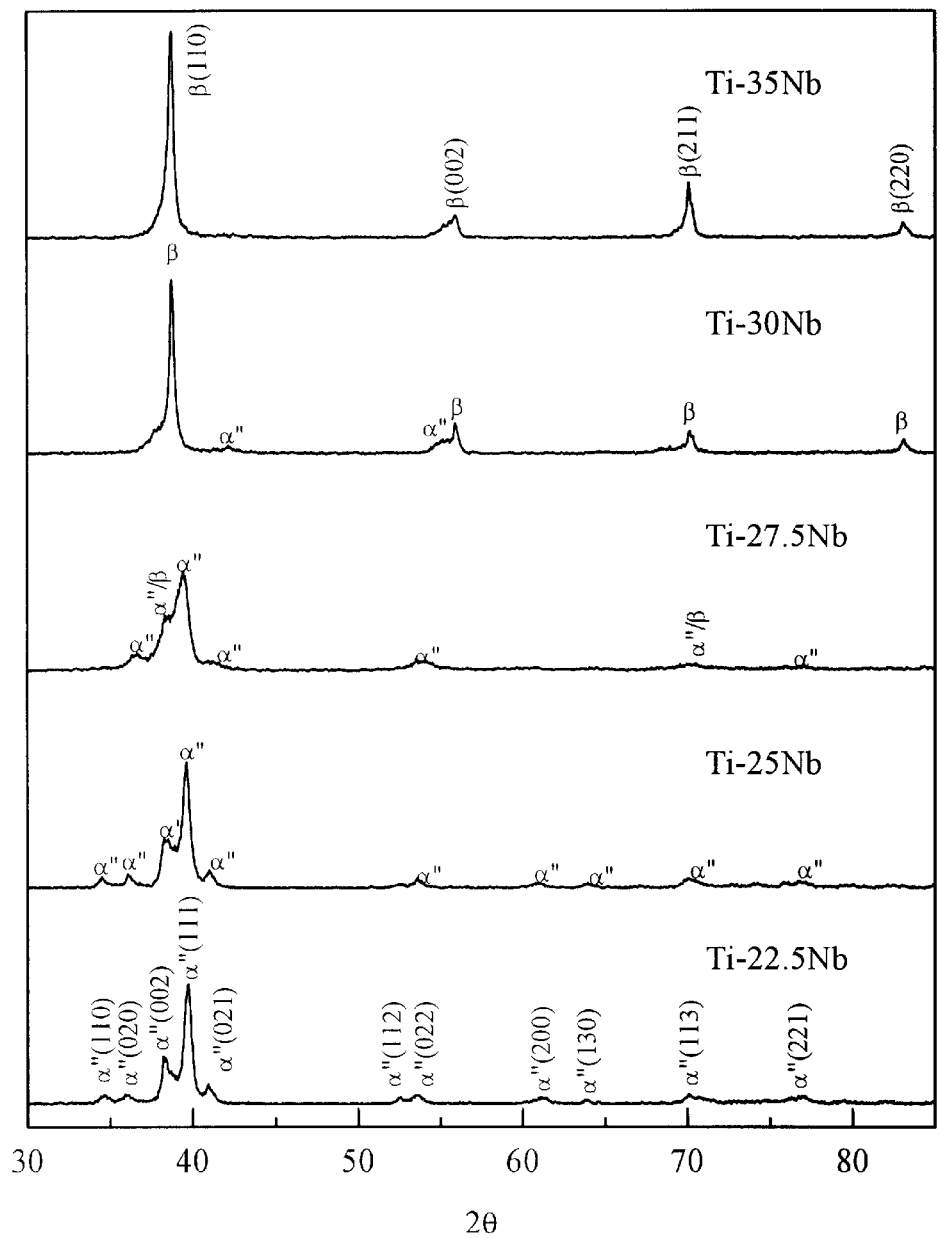

X-ray diffraction (XRD) for phase analysis was conducted using a Rigaku diffractometer (Rigaku D-max IIIV, Rigaku Co., Tokyo, Japan) operated at 30 kV and 20 mA. A Ni-filtered CuK$_\alpha$ radiation was used for this study. A silicon standard was used for calibration of diffraction angles. Scanning speed of 1°/min was used. The phases were identified by matching each characteristic peak in the diffraction pattern with the JCPDS files. The results are shown in FIG. 1, and are summarized in Table 2.

TABLE 2

| Sample code | Phase | Crystal structure |
|---|---|---|
| c.p. Ti | α' | Hexagonal |
| Ti-5 Nb | α' | Hexagonal |
| Ti-10 Nb | α' | Hexagonal |
| Ti-15 Nb | α'/α" | Hexagonal/orthorhombic |
| Ti-17.5 Nb | α" | Orthorhombic |
| Ti-20 Nb | α" | Orthorhombic |
| Ti-22.5 Nb | α" | Orthorhombic |
| Ti-25 Nb | α" | Orthorhombic |
| Ti-27.5 Nb | α"/β | Orthorhombic/bcc |
| Ti-30 Nb | α"/β | Orthorhombic/bcc |
| Ti-35 Nb | β | bcc |

Three-point bending tests were performed using a desktop mechanical tester (Shimadzu AGS-500D, Tokyo, Japan) operated at 0.5 mm/sec. Reduced size (36×5×1 mm) specimens were cut from the castings and polished using sand paper to a #1000 level. The bending strengths were determined using the equation, $$\sigma = 3PL/2bh^2$$

where σ is bending strength (MPa); P is load (Kg); L is span length (mm); b is specimen width (mm) and h is specimen thickness (mm). The modulus of elasticity in bending was calculated from the load increment and the corresponding deflection increment between the two points on a straight line as far apart as possible using the equation, $$E = L^3 \Delta P / 4bh^3 \Delta \delta$$

where E is modulus of elasticity in bending (Pa); ΔP is load increment as measured from preload (N); and Δδ is deflection increment at midspan as measured from preload. The average bending strength and modulus of elasticity in bending were taken from at least six tests under each condition.

Figure 2:
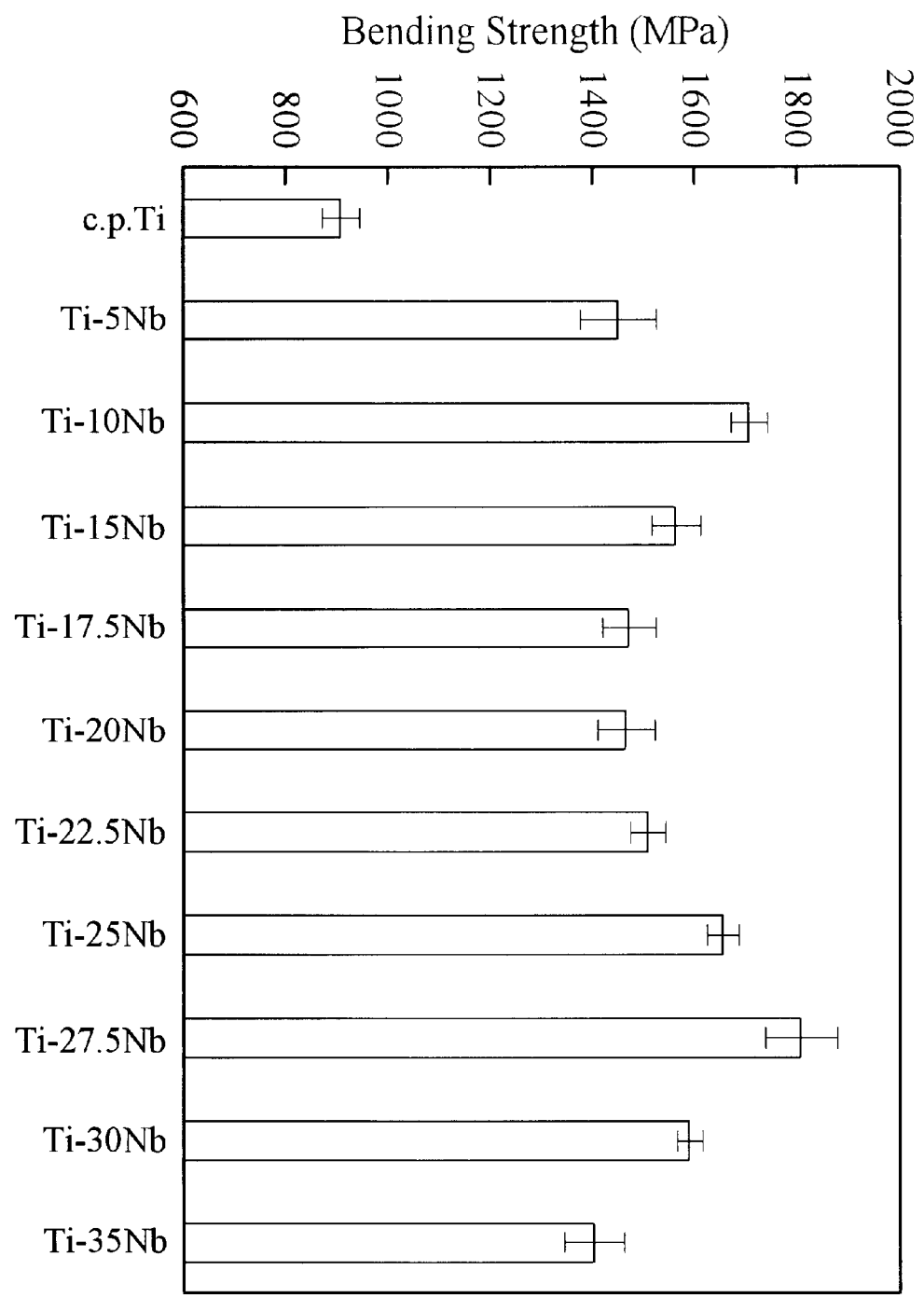
FIG. 2 is a plot showing, the bending strength of the c.p. Ti and the binary Ti—Nb alloys of the present invention, Ti-5Nb, Ti-10Nb, Ti-15Nb, Ti-17.5Nb, Ti-20Nb, Ti-22.5Nb, Ti-25Nb, Ti-27.5Nb, Ti-30Nb, and Ti-35Nb.
Figure 3:
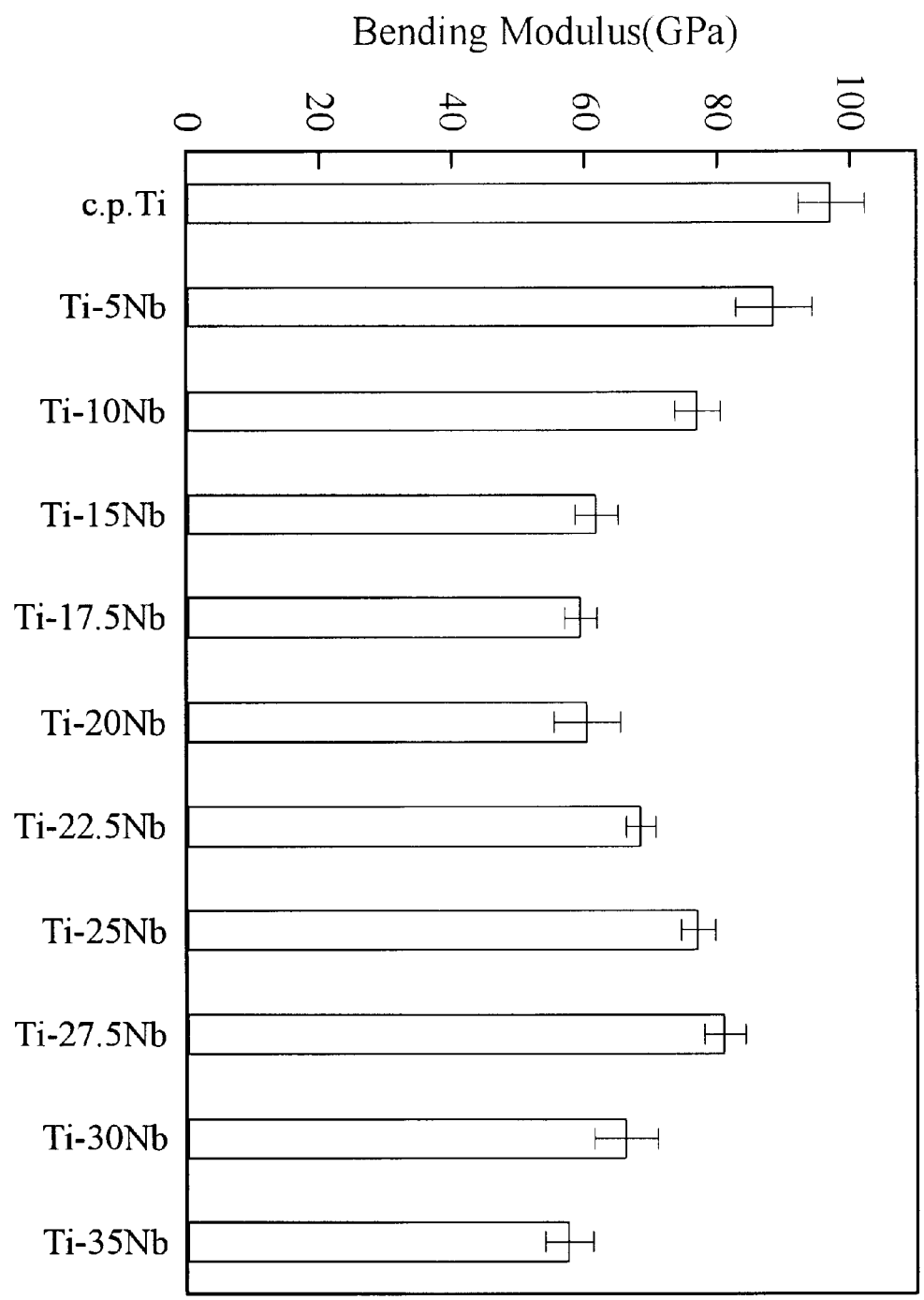
FIG. 3 is a plot showing the elastic modulus of the c.p. Ti and the binary Ti—Nb alloys of the present invention, Ti-5Nb, Ti-10Nb, Ti-15Nb, Ti-17.5Nb, Ti-20Nb, Ti-22.5Nb, Ti-25Nb, Ti-27.5Nb, Ti-30Nb, and Ti-35Nb.

The comparison of the bending strength and modulus of the Ti—Nb alloys prepared in the present invention together with c.p. Ti are shown in FIGS. 2 and 3.

Figure 4:
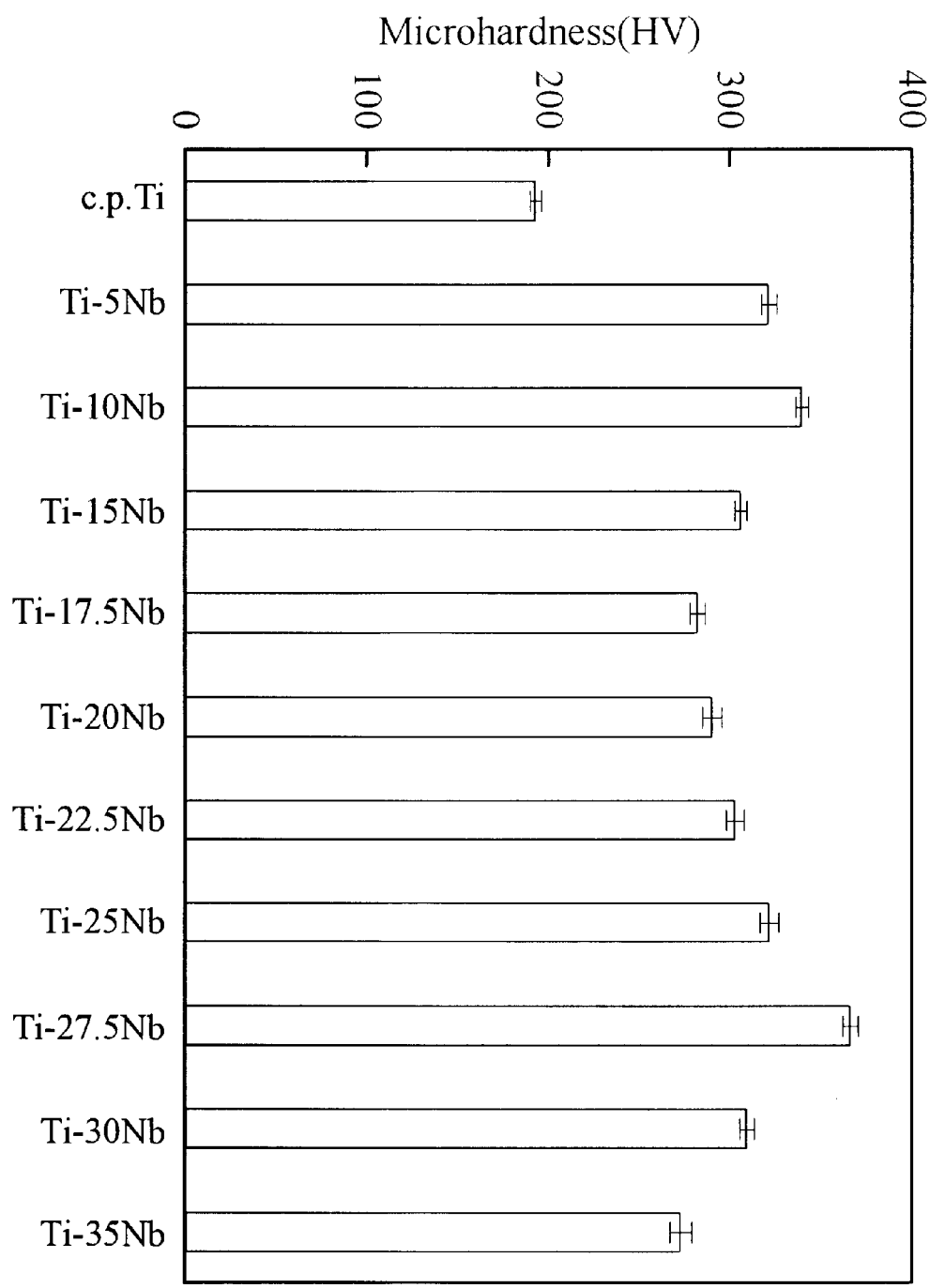
FIG. 4 is a plot showing the microhardness of the c.p. Ti and the binary Ti—Nb alloys of the present invention, Ti-5Nb, Ti-10Nb, Ti-15Nb, Ti-17.5Nb, Ti-20Nb, Ti-22.5Nb, Ti-25Nb, Ti-27.5Nb, Ti-30Nb, and Ti-35Nb.

The microhardness of polished alloys was measured using a Matsuzawa MXT70 microhardness tester at 200 gm for 15 seconds. The results are shown in FIG. 4.

The inventors have gathered mechanical properties of several well known c.p. Ti and Ti alloys, which are listed in the following Table 3 together with those of the biocompatible binary Ti—Nb alloys of the present invention.

TABLE 3

| Property Cast alloy | Hardness (HV) | Bending strength (MPa) | Bending modulus (GPa) | Major phase | Strength/ modulus ×1000 |
|---|---|---|---|---|---|
| c.p. Ti (Grade 2) | 156 | 884 | 92 | α' | 9.6 |
| c.p. Ti (Grade 4) |  | 1315 | 110 | α' | 11.9 |
| Ti-15Mo | 307 | 1348 | 71 | β | 19.0 |
| Ti-6Al-4V | 294 | 1857 | 105 | α' + β | 17.7 |
| Ti-13Nb-13Zr | 285 | 1471 | 66 | α' + β | 22.3 |
| Ti-7Mo-7Hf |  | 1299 | 67 | β | 19.4 |
| Ti-35.3Nb-5.7Ta-7.3Zr |  | 1133 | 63 | β | 18.0 |
| Ti-15Nb | 307 | 1565 | 61.8 | α" | 25.3 |
| Ti-20Nb | 292 | 1466 | 60.4 | α" | 24.3 |
| Ti-25Nb | 327 | 1656 | 77.1 | α" | 21.5 |

It can be seen from Table 3 that the biocompatible binary Ti—Nb alloys of the present invention have a high bending strength and a low modulus (high strength/modulus ratios) compared to the prior art Ti alloys.

Table 4 lists the critical anodic current density ($I_{corr}$) of the c.p. Ti and selected Ti—Nb alloys of the present invention obtained from the potentiodynamic polarization profiles thereof in 37° C. Hanks' solution.

It can be seen from Table 4 that all the alloys have an excellent corrosion resistance.

TABLE 4

|  | c.p. Ti | Ti-5Nb | Ti-17.5Nb | Ti-27.5Nb | Ti-35Nb |
|---|---|---|---|---|---|
| $I_{corr}$ (μA/cm$^2$) | 0.629 | 1.256 | 0.782 | 0.645 | 2.239 |

Although the present invention has been described with reference to specific details of certain embodiments thereof, it is not intended that such details should be regarded as limitations upon the scope of the invention except as and to the extent that they are included in the accompanying claims. Many modifications and variations are possible in light of the above disclosure.

What is claimed is:

1. A medical implant consisting essentially of biocompatible titanium-niobium (Ti—Nb) alloy containing α"phase as a major phase, said alloy consisting essentially of 13–28 wt % of Nb, and the balance titanium.

2. The medical implant according to claim 1, wherein said alloy further comprises one or more incidental impurities selected from the group consisting of carbon, oxygen and nitrogen, wherein a total amount of said one or more incidental impurities is less than 1 wt %.

3. The medical implant according to claim 1 which is an orthopedic implant.

4. The medical implant according to claim 1 which is a dental implant, dental crown, dental bridge or a denture framework.

* * * * *